United States Patent
Kitadume et al.

(10) Patent No.: US 9,580,524 B2
(45) Date of Patent: Feb. 28, 2017

(54) VINYLCYCLOPROPANE, MONOMER COMPOSITION, POLYMER, POLYMER COMPOSITION, AND ARTICLE

(71) Applicant: Dexerials Corporation, Shinagawa-ku, Tokyo (JP)

(72) Inventors: Koji Kitadume, Tokyo (JP); Hiroto Chiba, Tokyo (JP); Tetsuya Abe, Tokyo (JP); Tomoyasu Sunaga, Tokyo (JP); Takeshi Endo, Yokohama (JP)

(73) Assignee: Dexerials Corporation, Shinagawa-ku, Tokyo (JP)

( * ) Notice: Subject to any disclaimer, the term of this patent is extended or adjusted under 35 U.S.C. 154(b) by 0 days.

(21) Appl. No.: 15/124,798

(22) PCT Filed: Feb. 24, 2015

(86) PCT No.: PCT/JP2015/056017
§ 371 (c)(1),
(2) Date: Sep. 9, 2016

(87) PCT Pub. No.: WO2015/137173
PCT Pub. Date: Sep. 17, 2015

(65) Prior Publication Data
US 2017/0022302 A1 Jan. 26, 2017

(30) Foreign Application Priority Data

Mar. 11, 2014 (JP) .................................. 2014-048153

(51) Int. Cl.
C08F 22/14 (2006.01)
C07C 69/743 (2006.01)
C07C 69/753 (2006.01)
C08G 61/00 (2006.01)
C07C 13/615 (2006.01)

(52) U.S. Cl.
CPC ............ C08F 22/14 (2013.01); C07C 69/753 (2013.01); C07C 2101/02 (2013.01); C07C 2103/74 (2013.01)

(58) Field of Classification Search
CPC ..... C07C 13/615; C07C 69/743; C08G 61/00; C08F 22/10
USPC ............ 526/282; 560/124, 125; 585/22, 352
See application file for complete search history.

(56) References Cited

U.S. PATENT DOCUMENTS 4,391,823 A 7/1983 Boxler et al.
5,886,212 A * 3/1999 Rheinberger .......... A61K 6/083
526/308

FOREIGN PATENT DOCUMENTS

JP H1045661 A 2/1998
JP 2010260945 A 11/2010
JP 2010260946 A 11/2010

OTHER PUBLICATIONS

Okazaki, et al, "Synthesis and Radical Ring-Opening Polymerization Behavior of Bifunctional Vinylcyclopropane Bearing a Spiroacetal Moiety," Macromolecules 1995, 28, 6026-6028.*
Jun. 2, 2015, International Search Report issued in the International Patent Application No. PCT/JP2015/056017.
Jun-ichi Sugiyama et al., Free Radical Ring-Opening Polymerization of 1, 1-Bis[(1-adamantyloxy) carbonyl]-2-vinylcyclopropane, Macromolecules, 1996, vol. 29, No. 6, 1943-1950.
N. Moszner et al., Macromol. Rapid Commun., 1997, 18, 775-780.
Norbert Moszner et al., Polymerization of Cyclic Monomer. VII. Synthesis and Radical Polymerization of 1, 3-Bis [(1-alkoxycarbonyl-2-vinylcyclopropane-1-yl)carboxy] benzenes, Journal of Applied Polymer Science, 1999, vol. 72, 1775-1782.
Ueda et al., Macromolecules, 27, 5543 (1994).

* cited by examiner

*Primary Examiner* — Fred M Teskin
(74) *Attorney, Agent, or Firm* — Kenja IP Law PC

(57) ABSTRACT

Provided are a vinylcyclopropane that exhibits volume expansion upon homopolymerization and that enables improved solvent solubility, a monomer composition that contains the vinylcyclopropane, a polymer of the vinylcyclopropane, a polymer composition that contains the polymer, and an article that is obtainable through curing of the monomer composition. The vinylcyclopropane is represented by general formula (I) shown below.

[CHEM. 1]

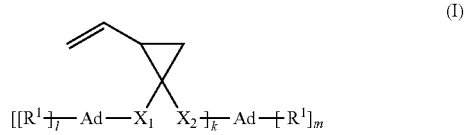

(I)

15 Claims, 4 Drawing Sheets
(4 of 4 Drawing Sheet(s) Filed in Color)

VINYLCYCLOPROPANE, MONOMER COMPOSITION, POLYMER, POLYMER COMPOSITION, AND ARTICLE

CROSS-REFERENCE TO RELATED APPLICATION

The present application claims priority of Japanese Patent Application No. 2014-048153 (filed on Mar. 11, 2014), the entire disclosure of which is incorporated into the present application by reference.

TECHNICAL FIELD

The present disclosure relates to a vinylcyclopropane, a monomer composition, a polymer, a polymer composition, and an article, and in particular relates to a vinylcyclopropane, a monomer composition containing the vinylcyclopropane, a polymer of the vinylcyclopropane, a polymer composition containing the polymer, and an article obtainable through curing of the monomer composition.

BACKGROUND

Vinyl monomers (acrylic materials, etc.) and thermosetting resins (epoxy resins, phenolic resins, etc.) are conventionally used as adhesive materials.

However, volume shrinkage occurs during polymerization of such vinyl monomers and thermosetting resins, which leads to problems such as residual internal stress, cracking, and reduced adhesive strength.

The use of cyclic monomers as adhesive materials is being investigated with the aim of resolving the problems described above. Cyclic monomers are known to exhibit a smaller degree of polymerization shrinkage than vinyl monomers of equivalent molecular mass. Known examples of such cyclic monomers include vinylcyclopropanes, vinyloxiranes, 4-methylene-1,3-dioxolanes, cyclic ketene acetals, benzocyclobutenes, spiro orthocarbonates, spiro orthoesters, vinylcyclopropane cyclic acetals, cyclic allyl sulfides, and cyclic vinyl sulfones.

Among such cyclic monomers, vinylcyclopropanes are attracting particular attention. For example, a technique that involves using a polymer (homopolymer or copolymer) of a multifunctional vinylcyclopropane monomer (structural formula (1) shown below) as a dental material has been investigated (for example, refer to PTL 1). PTL 1 discloses that a copolymer of urethane dimethacrylate used as a vinyl monomer and a bis(vinylcyclopropane) used as a multifunctional vinylcyclopropane has improved mechanical properties and polymerization shrinkage compared to a copolymer of urethane dimethacrylate and dodecanediol dimethacrylate and a copolymer of urethane dimethacrylate and 1,1-bis(phenoxycarbonyl)-2-vinylcyclopropane.

[CHEM. 1]

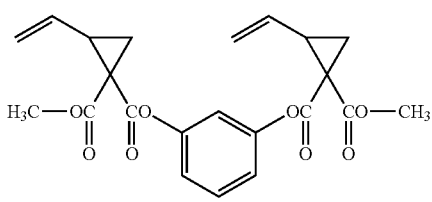

(1)

However, materials based on vinyl monomers (acrylic materials, etc.) exhibit noticeably high polymerization shrinkage. Consequently, when the multifunctional vinylcyclopropane monomer described in PTL 1 is copolymerized with a material based on a vinyl monomer (acrylic material, etc.), there is a problem that polymerization shrinkage cannot be sufficiently suppressed, and it is thought that in such a situation, a monomer that exhibits as large a degree of volume expansion as possible is beneficial.

Compounds represented by structural formulae (2) to (4) shown below are also known multifunctional vinylcyclopropanes (for example, refer to NPL 1 and 2).

The compound represented by structural formula (2) shown below (volume change upon homopolymerization: −2.8%) and the compound represented by structural formula (4) shown below (volume change upon homopolymerization: −3.8%) have bulky substituents and exhibit a smaller degree of polymerization shrinkage than the compound represented by structural formula (3) shown below (volume change upon homopolymerization: −7.0%).

However, the fact that the compound represented by structural formula (2) shown below and the compound represented by structural formula (4) shown below do not exhibit volume expansion upon homopolymerization is a problem.

Up until the present time, a vinylcyclopropane that has a multifunctional structure and that also exhibits relatively large expansion has not been commonly known.

[CHEM. 2]

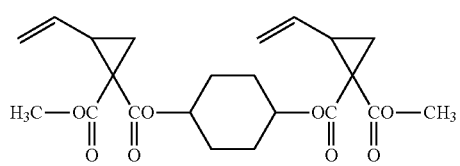

(2)

[CHEM. 3]

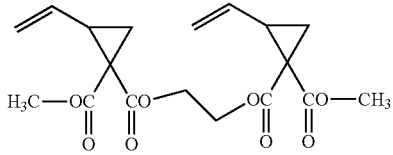

(3)

[CHEM. 4]

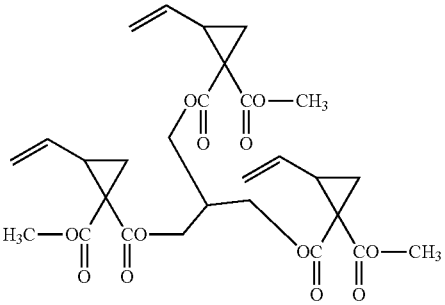

(4)

Furthermore, a monofunctional vinylcyclopropane that has adamantyl groups and that is represented by structural formula (5) shown below is a known example of a monofunctional vinylcyclopropane having bulky substituents that is a compound exhibiting excellent volume expansion (for example, refer to NPL 3).

[CHEM. 5]

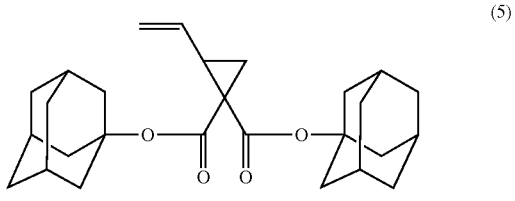

(5)

However, the poor solubility of the compound represented by structural formula (5) in solvents such as acetone is problematic. Accordingly, a complicated process is required in production in order to obtain a polymer, which means that the aforementioned compound suffers from a problem of being disadvantageous in terms of convenience as a monomer.

Furthermore, a monofunctional vinylcyclopropane having an alicyclic compound introduced as a bulky substituent is known and variation of the number of ring members has been investigated (for example, refer to PTL 2 and 3).

Monomers described in PTL 2 and 3 suffer from a problem that despite polymerization shrinkage being mitigated, they do not exhibit volume expansion upon homopolymerization As described above, a compound that exhibits volume expansion upon homopolymerization, maintains mechanical properties, and is highly convenient in production has yet to be developed and there is strong demand for development of such a compound.

CITATION LIST

Patent Literature

PTL 1: JP H10-45661 A
PTL 2: JP 2010-260945 A
PTL 3: JP 2010-260946 A

Non-Patent Literature

NPL 1: N. Moszner et al., Journal of Applied Polymer Science, 1999, 72, 1775-1782
NPL 2: N. Moszner et al., Macromol. Rapid Commun., 1997, 18, 775-780
NPL 3: Ueda et al., Macromolecules, 27, 5543 (1994)

SUMMARY

Technical Problem

The present disclosure is directed toward solving the various conventional problems described above and achieving the following objective. Specifically, an objective of the present disclosure is to provide a vinylcyclopropane that exhibits volume expansion upon homopolymerization and that enables improved solvent solubility, a monomer composition containing the vinylcyclopropane, a polymer of the vinylcyclopropane, a polymer composition containing the polymer, and an article obtainable through curing of the monomer composition.

Solution to Problem

The following is provided as a solution to the problem described above. Specifically, the present disclosure provides:

<1> A vinylcyclopropane represented by general formula (I) shown below

[CHEM. 6]

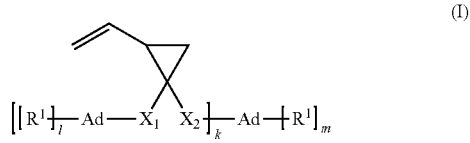

(I)

where, in general formula (I):

$R^1$ represents —H, —OH, —$NH_2$, —$NO_2$, —COOR, —CN, =O, —OCOCH=$CH_2$, —OCO($CH_3$)C=$CH_2$, a halogen, an alkylene group having a carbon number of 1-20, a cycloalkylene group having a carbon number of 3-20, an arylene group having a carbon number of 6-14, or any one of an alkylene group having a carbon number of 1-20, a cycloalkylene group having a carbon number of 3-20, or an arylene group having a carbon number of 6-14 that is interrupted by O, S, N, or NH;

$X_1$ represents CO, CO—O, O—CO, CO—S, S—CO, CO—NR, NR—CO, O, S, $SO_2$, or a single bond;

$X_2$ represents CO, CO—O, O—CO, CO—S, S—CO, CO—NR, NR—CO, O, S, $SO_2$, or a single bond;

for $R^1$, $X_1$, and $X_2$, R represents H, an alkyl group having a carbon number of 1-6, a cycloalkylene group having a carbon number of 3-6, an aryl group having a carbon number of 6-14, or a heterocyclic group having a carbon number of 6-14;

k represents an integer of 2-4;
l represents an integer of 1-9;
m represents an integer of 1-8; and
Ad represents an adamantyl group.

The vinylcyclopropane described above in <1>, which is a compound represented by general formula (I), exhibits volume expansion upon homopolymerization and enables improved solvent solubility.

<2> The vinylcyclopropane described above in <1>, wherein $X_1$ and $X_2$ are each an ester.
<3> The vinylcyclopropane described above in <1> or <2>, wherein k is 2.
<4> A monomer composition containing the vinylcyclopropane described above in any one of <1> to <3>.
<5> A polymer of the vinylcyclopropane described above in any one of <1> to <3>.
<6> The polymer described above in <5>, wherein the polymer exhibits a volume change of at least +5.0% relative to monomer volume of the vinylcyclopropane.
<7> The polymer described above in <5>, wherein the polymer is a copolymer of the vinylcyclopropane and a polymerizable compound other than the vinylcyclopropane.
<8> A polymer composition containing the polymer described above in any one of <5> to <7>.
<9> An article obtainable through curing of the monomer composition described above in <4>.

Advantageous Effect

According to the present disclosure, it is possible to solve the various conventional problems described above and achieve the objective described above, and it is also possible to provide a vinylcyclopropane that exhibits volume expansion upon homopolymerization and that enables improved solvent solubility, a monomer composition containing the vinylcyclopropane, a polymer of the vinylcyclopropane, a polymer composition containing the polymer, and an article obtainable through curing of the monomer composition.

BRIEF DESCRIPTION OF THE DRAWINGS

The patent or application file contains at least one drawing executed in color. Copies of this patent or patent application publication with color drawing(s) will be provided by the Office upon request and payment of the necessary fee. In the accompanying drawings.

Figure 1:
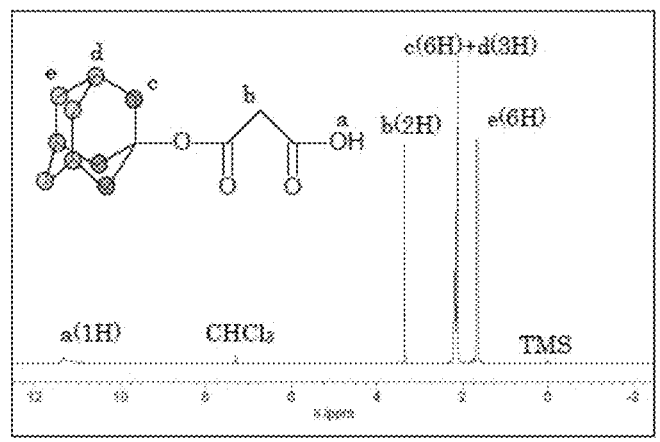
FIG. 1 is a $^1$H-NMR chart of O-adamantylmalonic acid (Ad-COOH) in Example 1.

DETAILED DESCRIPTION (Vinylcyclopropane)
A presently disclosed vinylcyclopropane is a compound represented by general formula (I) shown below.

[CHEM. 7]

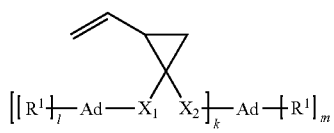

(I)

The following explains $R^1$, $X_1$, $X_2$, k, l, m, and Ad in general formula (I).

<$R^1$>
$R^1$ can be appropriately selected depending on the objective without any specific limitations other than being —H, —OH, —NH$_2$, —NO$_2$, —COOR, —CN, =O, —OCOCH=CH$_2$, —OCO(CH$_3$)C=CH$_2$, a halogen, an alkylene group having a carbon number of 1-20, a cycloalkylene group having a carbon number of 3-20, an arylene group having a carbon number of 6-14, or any one of an alkylene group having a carbon number of 1-20, a cycloalkylene group having a carbon number of 3-20, or an arylene group having a carbon number of 6-14 that is interrupted by O, S, N, or NH. R can be appropriately selected depending on the objective without any specific limitations other than being H, an alkyl group having a carbon number of 1-6, a cycloalkylene group having a carbon number of 3-6, an aryl group having a carbon number of 6-14, or a heterocyclic group having a carbon number of 6-14.

<$X_1$>
$X_1$ can be appropriately selected depending on the objective without any specific limitations other than being CO, CO—O, O—CO, CO—S, S—CO, CO—NR, NR—CO, O, S, SO$_2$, or a single bond, where R is H, an alkyl group having a carbon number of 1-6, a cycloalkylene group having a carbon number of 3-6, an aryl group having a carbon number of 6-14, or a heterocyclic group having a carbon number of 6-14.

From among the above, $X_1$ is preferably an ester (i.e., CO—O or O—CO).

<$X_2$>
$X_2$ can be appropriately selected depending on the objective without any specific limitations other than being CO, CO—O, O—CO, CO—S, S—CO, CO—NR, NR—CO, O, S, SO$_2$, or a single bond, where R is H, an alkyl group having a carbon number of 1-6, a cycloalkylene group having a carbon number of 3-6, an aryl group having a carbon number of 6-14, or a heterocyclic group having a carbon number of 6-14.

From among the above, $X_2$ is preferably an ester (i.e., CO—O or O—CO).

<k>
The value of k can be appropriately selected depending on the objective without any specific limitations other than being an integer of 2-4, and is preferably 2.

It is advantageous for k to be at least 2 from a viewpoint of solubility since solubility in solvents is low if k is 1. However, a complicated process is required for synthesis if k is greater than 4.

<l>
The value of l can be appropriately selected depending on the objective without any specific limitations other than being an integer of 1-9.

<m>
The value of m can be appropriately selected depending on the objective without any specific limitations other than being an integer of 1-8.

<Ad>
Ad represents an adamantyl group. The adamantyl group is a functional group of adamantane.

It is advantageous that the presently disclosed vinylcyclopropane has adamantyl groups introduced therein in terms that ring-opening polymerization can occur with a high conversion rate and without being easily influenced by polymerization conditions.

The vinylcyclopropane can be appropriately selected depending on the objective without any specific limitations other than being a compound represented by general formula (I). Specific examples include 1,3-bis[(1-adamantyloxycarbonyl-2-vinylcyclopropane-1-yl)carbonyloxy]adamantane (Ad-MVCP) (compound represented by structural formula (6) shown below), 1,3,5-tris[(1-adamantyloxycarbonyl-2-vinylcyclopropane-1-yl)carbonyloxy]adamantane, and
1,3,5,7-tetra[(1-adamantyloxycarbonyl-2-vinylcyclopropane-1-yl)carbonyloxy]adamantane.

[CHEM. 8]

(6)

(Monomer Composition)

A presently disclosed monomer composition contains at least the vinylcyclopropane described above and may further contain other components as required.

<Other Components>

The other components can be appropriately selected depending on the objective without any specific limitations and examples thereof include polymerizable compounds other than the vinylcyclopropane, solvents, polymerization initiators, fillers, stabilizers, UV absorbers, flame retardants, plasticizers, dyes, and pigments. Any one of such other components may be used individually or any two or more of such other components may be used together.

—Polymerizable Compounds Other than the Vinylcyclopropane—

Polymerizable compounds other than the vinylcyclopropane can be appropriately selected depending on the objective without any specific limitations and examples thereof include vinyl compounds, diene compounds, and non-vinyl compounds. Any one of such polymerizable compounds may be used individually or any two or more of such polymerizable compounds may be used together.

--Vinyl Compounds--

Vinyl compounds can be appropriately selected depending on the objective without any specific limitations and examples thereof include methyl (meth)acrylate, ethyl (meth)acrylate, butyl (meth)acrylate, benzyl (meth)acrylate, furfuryl (meth)acrylate, phenyl (meth)acrylate, 2-hydroxyethyl (meth)acrylate, propyl (meth)acrylate, mesityl methacrylate, 2-(methoxymethyl)acrylic acid, 2-(ethoxymethyl) acrylic acid, 2-(hydroxymethyl)acrylic acid, N-ethylacrylamide, N,N'-dimethylacrylamide, N-(2-hydroxyethyl)acrylamide, N-methyl-N-(2-hydroxyethyl)acrylamide, N-ethylmethacrylamide, N-(2-hydroxyethyl)methacrylamide, N-vinylpyrrolidone, allyl ether, bisphenol A di(meth)acrylate, bis-GMA (addition product of methacrylic acid and bisphenol A diglycidyl ether), UDMA (addition product of 2-hydroxyethyl methacrylate and 2,2,4-trimethylhexamethylene diisocyanate), diethylene glycol di(meth)acrylate, triethylene glycol di(meth)acrylate, tetraethylene glycol di(meth)acrylate, trimethylolpropane tri(meth)acrylate, pentaerythritol tetra(meth)acrylate, butanediol di(meth)acrylate, 1,10-decanediol di(meth)acrylate, 1,12-dodecanediol di(meth)acrylate, tricyclodecane dimethanol dimethacrylate, tris(2-hydroxyethyl) isocyanuric acid or acrylic acid ester, 9,9-bis[4-(2-acryloylethoxy)phenyl]fluorene, N-(2-hydroxyethyl)acrylamide, ethylene, styrene, vinyl chloride, butadiene, vinyl acetate, allyl alcohol, allyl amine, allyl bromide, allyl chloride, allyl ether, allyl sulfide, allicin, allyl disulfide, and allyl isothiocyanate. Any one of such vinyl compounds may be used individually or any two or more of such vinyl compounds may be used together.

--Diene Compounds--

Diene compounds can be appropriately selected depending on the objective without any specific limitations and examples thereof include natural rubber (NR), isoprene rubber (IR), butadiene rubber (BR), styrene butadiene rubber (SBR), chloroprene rubber (CR), acrylonitrile butadiene rubber (ABR), butadiene latex, and acrylonitrile butadiene styrene resin (ABS resin). Any one of such diene compounds may be used individually or any two or more of such diene compounds may be used together.

—Solvents—

Solvents can be appropriately selected depending on the objective without any specific limitations and examples thereof include lower alcohols, aromatic hydrocarbons, alicyclic hydrocarbons, aliphatic hydrocarbons, esters, ketones, amides, and ethers. Any one of such solvents may be used individually or any two or more of such solvents may be used together.

Among such solvents, aromatic hydrocarbons are preferable from a viewpoint of achieving a good conversion rate.

—Polymerization Initiators—

Polymerization initiators can be appropriately selected depending on the objective without any specific limitations and examples thereof include azo compounds, organic peroxides, and photoinitiators. Any one of such polymerization initiators may be used individually or any two or more of such polymerization initiators may be used together.

--Azo Compounds--

Azo compounds can be appropriately selected depending on the objective without any specific limitations and examples thereof include azobis(isobutyronitrile) (AIBN) and azobis(4-cyanovaleric acid).

--Organic Peroxides--

Organic peroxides can be appropriately selected depending on the objective without any specific limitations and examples thereof include benzoyl peroxide, dilauroyl peroxide, tert-butyl peroxide, benzopinacol, and 2,2'-dialkylbenzopinacol.

--Photoinitiators--

Photoinitiators can be appropriately selected depending on the objective without any specific limitations other than being suitable for UV or visible region light and examples thereof include benzoin ether, dialkylbenzeneketal, dialkoxyacetophenone, acyl or bisacylphosphine oxide, α-diketones (for example, 9,10-phenanthraquinone), diacetyl, furil, anisil, 4,4'-dichlorobenzil, 4,4'-dialkoxybenzil, and camphorquinone.

Any one of such polymerization initiators may be used individually or any two or more of such polymerization initiators may be used together. For example, in order to promote a polymerization reaction, an organic peroxide (for example, benzoyl peroxide or lauroyl peroxide), an α-diketone (for example, camphorquinone), and an aromatic amine (for example, N,N'-dimethyl-p-toluidine, N,N'-dihydroxyethyl-p-toluidine, or ethyl p-dimethylaminobenzoate) are preferably used in combination. Furthermore, a reductant (for example, ascorbic acid, a barbiturate, or a sulfinic acid) may be used too as required.

—Fillers—

Fillers are Used in Order to Enhance Mechanical Properties.

Fillers can be appropriately selected depending on the objective without any specific limitations and examples thereof include inorganic particle fillers (for example, an amorphous spherical material based on an oxide), fine fillers (for example, pyrogenic silica or precipitated silica), macro- and mini-fillers (for example, quartz powder, glass ceramic powder, or glass powder having an average particle size of from 0.01 μm to 5 μm), radiopaque fillers (for example, ytterbium trifluoride), glass fiber, polyamide fiber, and carbon fiber. Any one of such fillers may be used individually or any two or more of such fillers may be used together.

—Stabilizers—

Stabilizers can be appropriately selected depending on the objective without any specific limitations and examples thereof include hydroquinone (HQ); hydroquinone monomethyl ether (HQME); 4-tert-butylcatechol (TBC); hindered amine light stabilizers such as ADK STAB LA62 and ADK STAB LA67 (produced by ADEKA Corporation), and TINUVIN 765, TINUVIN 144, TINUVIN 770, and TINUVIN 622 (produced by BASF Japan); and blend light stabilizers such as TINUVIN B75 and TINUVIN PUR866 (produced by BASF Japan). Any one of such stabilizers may be used individually or any two or more of such stabilizers may be used together.

—UV Absorbers—

UV absorbers can be appropriately selected depending on the objective without any specific limitations and examples thereof include benzophenone UV absorbers; benzotriazole UV absorbers; triazine UV absorbers; cyanoacrylate UV absorbers; TINUVIN 213, TINUVIN 234, TINUVIN 326, TINUVIN 571, and the like (produced by BASF Japan); and ADK STAB LA29, ADK STAB LA31, LA31RG, LA31G, LA-32, LA36, LA36RG, LA-46, 1413, LA-F70, and the like (produced by Adeka Argus Chemical Co., Ltd.). Any one of such UV absorbers may be used individually or any two or more of such UV absorbers may be used together.

—Other Components—

Other components can be appropriately selected depending on the objective without any specific limitations and examples thereof include flame retardants, plasticizers, dyes, and pigments. Any one of such other components may be used individually or any two or more of such other components may be used together.

(Polymer)

A presently disclosed polymer is a polymer of the presently disclosed vinylcyclopropane.

<Polymer>

The polymer may be a homopolymer of the vinylcyclopropane or a copolymer of the vinylcyclopropane and a polymerizable compound other than the vinylcyclopropane.

In a situation in which the presently disclosed polymer is a copolymer of the vinylcyclopropane and a polymerizable compound other than the vinylcyclopropane, the polymerizable compound other than the vinylcyclopropane may be the same as any of those previously explained.

<Volume Change Relative to Monomer Volume>

Volume change relative to monomer volume refers to the change in volume of the polymer relative to the volume of the monomer or monomers that are constituent components of the polymer. This volume change relative to monomer volume is obtained through the following equation by measuring the density of the monomer(s) at 25° C. prior to polymerization (monomer density) and the density of the polymer at 25° C. after polymerization (polymer density).

((Monomer density)−(Polymer density))/(Monomer density)×100(%)

If the resultant value for volume change (%) is positive, this indicates that volume expansion occurs in accompaniment to polymerization (i.e., volume expansion is exhibited upon polymerization). On the other hand, if the resultant value for volume change (%) is negative, this indicates that volume shrinkage occurs in accompaniment to polymerization (i.e., volume shrinkage is exhibited upon polymerization).

Although volume change relative to monomer volume can be appropriately selected depending on the objective without any specific limitations in a situation in which the polymer is a homopolymer of the vinylcyclopropane, the volume change is preferably at least +5.0%.

If volume change relative to monomer volume is less than +5.0% in a situation in which the polymer is a homopolymer, this means that volume shrinkage will be large in a situation in which the polymer is a copolymer. On the other hand, it is advantageous for volume change relative to monomer volume to be in the more preferable range or the particularly preferable range described above because in such a situation, the degree of volume change can be easily adjusted to within a desired range through copolymerization of the vinylcyclopropane with a polymerizable compound that exhibits large volume shrinkage, such as a vinyl compound.

(Polymer Composition)

A presently disclosed polymer composition contains at least the presently disclosed polymer and may further contain other components as required.

<Other Components>

Other components can be appropriately selected depending on the objective without any specific limitations and examples thereof include polymerizable compounds other than the vinylcyclopropane, solvents, polymerization initiators, fillers, stabilizers, UV absorbers, flame retardants, plasticizers, dyes, and pigments. Any one of such other components may be used individually or any two or more of such other components may be used together.

(Article)

A presently disclosed article is obtainable through curing of the presently disclosed monomer composition.

The article can be appropriately selected depending on the objective without any specific limitations other than being an article that is obtainable through curing of the presently disclosed monomer composition and examples thereof include optical materials, molding materials, composite materials, casting materials, sealing materials, medical materials, dental materials, recording materials, cements, coating materials, adhesives, and materials for holographic optical recording media.

<Curing>

The type of curing can be appropriately selected depending on the objective without any specific limitations and examples thereof include thermal curing and photo-curing. Any one of such types of curing may be used individually or any two or more of such types of curing may be used together.

—Thermal Curing—

Although the heating temperature during thermal curing can be appropriately selected depending on the objective without any specific limitations, the heating temperature is preferably from 60° C. to 180° C. A heating temperature of lower than 60° C. leads to a low conversion rate, whereas a heating temperature of higher than 180° C. leads to gradual pyrolysis. The heating time during thermal curing can be appropriately selected depending on the objective without any specific limitations.

EXAMPLES

The following provides more specific description of the present disclosure through examples and comparative examples. However, the present disclosure is not limited to the following examples.

Example 1

Synthesis of 1,3-bis[(1-adamantyloxycarbonyl-2-vinylcyclopropane-1-yl)carbonyloxy]adamantane (Ad-MVCP)

A compound represented by structural formula (6) shown below was produced through a first stage reaction, a second stage reaction, and a third stage reaction as shown in the following reaction scheme.

[CHEM. 9]

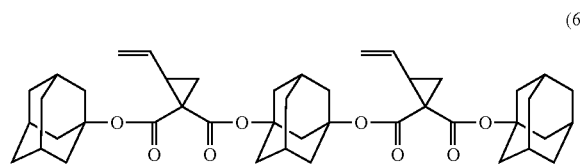

(6)

<<Reaction Scheme>>

[CHEM.10]

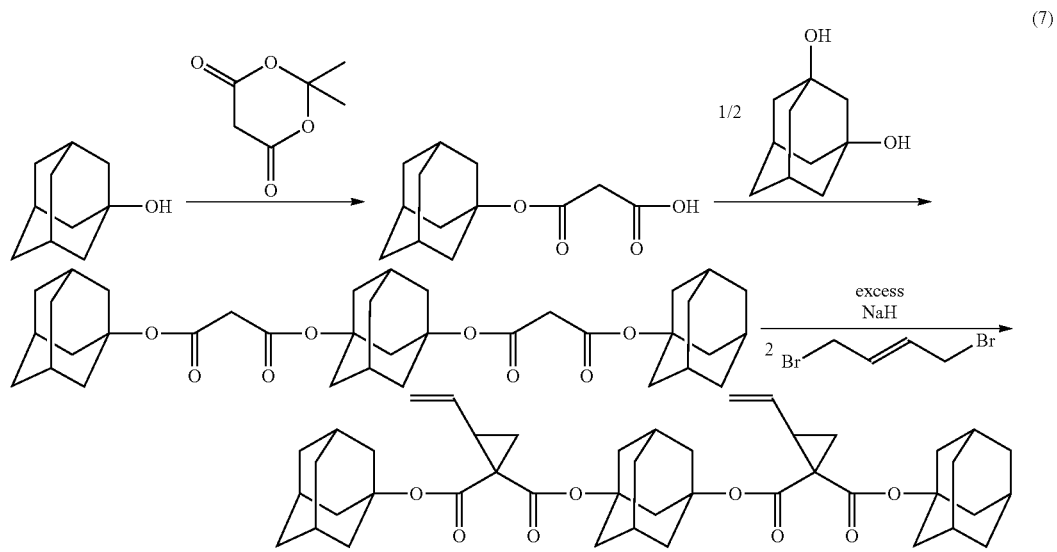

(7)

The following describes the first stage reaction, the second stage reaction, and the third stage reaction.

First Stage Reaction

Synthesis of O-adamantylmalonic acid (Ad-COOH)

A two-neck flask (100 mL) having a main tube provided with a Dimroth condenser having a three-way stop cock, a side tube sealed by a rubber septum cap, and a stirrer within the flask was heated using a heat gun while performing degassed drying using a vacuum pump to completely remove moisture attached to the surface of the apparatus. Thereafter, a gas collecting bag (or balloon) having nitrogen sealed therein was connected to the three-way stop cock and was used to introduce nitrogen into the reaction apparatus. Next, 9.14 g (60 mmol) of 1-adamantanol and 8.65 g (60 mmol) of Meldrum's acid were added from the side tube. Since there was a temporarily unsealed state during this addition, the addition was performed while compressing the gas collecting bag having nitrogen sealed therein in order to cause nitrogen to flow and prevent entry of air. After this addition, the side tube was resealed with the rubber septum, 60 mL of toluene (dehydrated) was added into the flask, and the flask was heated to 120° C. using an oil bath while being stirred using the stirrer. Once toluene reflux was confirmed, a reaction was carried out for 4 hours while maintaining toluene reflux. After the reaction, the flask contents were cooled to room temperature and transferred to a separating funnel in order to carry out extraction. Next, 600 mL of a saturated aqueous solution of sodium hydrogen carbonate was added to the separating funnel and liquid separation was carried out. After the separation, the product was present in an aqueous layer as a Na salt. The aqueous layer was dripped into 900 mL of 1N hydrochloric acid. Addition of the Na salt of the product into the hydrochloric acid caused a sodium carboxylate at the end thereof to be converted to a carboxylic acid. Since carbon dioxide gas was produced during the above, the resultant solution was left to stand for roughly 1 hour until gas production had subsided. The resultant solution had a large volume of 1,500 mL and was therefore transferred to a separating funnel in 500 mL portions, was subjected to extraction three times using 200 mL of dichloromethane, and the resultant organic layers were collected in a conical flask. Next, 1200 mL of the collected organic layers was dried for 30 minutes using magnesium sulfate (anhydrous). After performing filtration, solvent was evaporated using an evaporator. Thereafter, solvent was completely evaporated using a vacuum pump and cooling was performed in a refrigerator. As a result, the product (O-adamantylmalonic acid (Ad-COOH); compound represented by structural formula (8) shown below) was obtained as a white solid. The structure of the product was evaluated by NMR (FIGS. 1 and 2) and liquid chromatography-mass spectrometry (LC-MS) (FIG. 3), and the purity of the product was obtained from the area ratio in LC-MS (yield 93.7%, purity 100.0%).

[CHEM. 11]

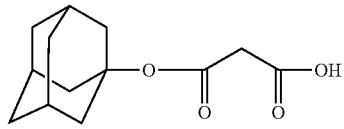

(8)

Second Stage Reaction

Synthesis of 1,3-bis[(1-adamantyloxycarbonyl)carbonyloxy]adamantane (Ad3)

A three-neck flask (1,000 mL) having a main tube provided with a dropping funnel covered at the top by a rubber septum, a side tube provided with a Dimroth condenser having a three-way stop cock, another side tube covered by a rubber septum, and a stirrer within the flask was heated with a heat gun while performing degassed drying using a vacuum pump to completely remove moisture attached to the surface of the apparatus. Thereafter, a gas collecting bag (or balloon) having nitrogen sealed therein was connected to the three-way stop cock and was used to introduce nitrogen into the reaction apparatus. Next, 12.0 g (50.39 mmol) of Ad-COOH and 4.236 g (25.18 mmol) of 1,3-adamantanediol were added from a side tube. Since there was a temporarily unsealed state during this addition, the addition was performed while compressing the gas collecting bag having nitrogen sealed therein in order to cause nitrogen to flow and prevent entry of air. After this addition, the side tube was resealed with the rubber septum, 540 mL of tetrahydrofuran (THF) (super dehydrated) was added, and vigorous stirring was performed for two hours at room temperature. Since the 1,3-adamantanediol had a very low tendency to dissolve, dissolution of the 1,3-adamantanediol was visually inspected during stirring and further stirring was performed if the 1,3-adamantanediol had not yet dissolved. Once the 1,3-adamantanediol had dissolved, the three-neck flask was placed in an ice bath for 10 minutes. The flask was held in the ice bath and was stirred while using the dropping funnel to drip in, over a period of 21 minutes, a THF (120 mL) solution of 10.40 g (50.41 mmol) of N,N'-dicyclohexylcarbodiimide (DCC) that was separately prepared in a degassing dried vessel. After the dripping, the ice bath was removed and a reaction was carried out for 3 hours at room temperature while stirring the flask. The reaction was tracked using thin layer chromatography (TLC) and LC-MS. Filtration was performed after the reaction because a large amount of a precipitated urea was present in the flask and the resultant solution was collected. Solvent was completely evaporated from the collected solution using an evaporator and a vacuum pump. The resultant crude product was purified by column chromatography (silica gel). The column chromatography was performed using an open column having a column tube diameter of 90 cm. In the column chromatography, the silica gel had a height of 300 mm (mass of silica gel approximately 1,200 g) and 9:1 toluene:diethyl ether was used as a developing solvent. The crude product was dissolved in 80 mL of the developing solvent. The column chromatography was performed with a column flow rate of 100 mL/30 minutes. The presence of the product in the resultant solution was confirmed by TLC. Solvent was completely evaporated from the solution that had passed through the column using an evaporator and a vacuum pump and cooling was performed using a refrigerator to obtain the product as a white solid. The structure of the product (1,3-bis[(1-adamantyloxy)carbonyloxy]adamantane (Ad3); compound represented by structural formula (9) shown below) was evaluated by NMR (FIGS. 4 and 5) and LC-MS (FIG. 6), and the purity of the product was obtained from the area ratio in LC-MS (yield 56.7%, purity 100.0%).

[CHEM. 12]

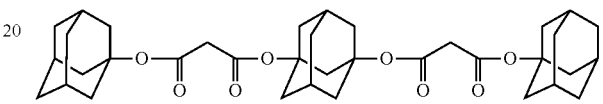

(9)

Third Stage Reaction

Synthesis of 1,3-bis[(1-adamantyloxycarbonyl-2-vinylcyclopropane-1-yl)carbonyloxy]adamantane (Ad-MVCP)

A three-neck flask (1,000 mL) having a main tube provided with a dropping funnel covered at the top by a rubber septum, a side tube provided with a Dimroth condenser having a three-way stop cock, another side tube covered by a rubber septum, and a stirrer within the flask was heated with a heat gun while performing degassed drying using a vacuum pump to completely remove moisture attached to the surface of the apparatus. Thereafter, a gas collecting bag (or balloon) having nitrogen sealed therein was connected to the three-way stop cock and was used to introduce nitrogen into the reaction apparatus. Next, 3.848 g of NaH (dispersed in liquid paraffin; amount of NaH 2.336 g, 97.36 mmol) was added from a side tube. Since there was a temporarily unsealed state during this addition, the addition was performed while compressing the gas collecting bag having nitrogen sealed therein in order to cause nitrogen to flow and prevent entry of air. After this addition, decantation was performed in order to remove the liquid paraffin added with the NaH. Decantation of the liquid paraffin was performed as follows. First, 480 mL of n-hexane (super dehydrated) was added into the flask and the flask was stirred for 30 minutes. Thereafter, since the washed NaH precipitated from the liquid paraffin after being left for 5 minutes, the supernatant was removed using a syringe. Washing was repeated in this manner three times. Next, the NaH was dried under reduced pressure using a vacuum pump. After the decantation described above, 5.624 g (26.29 mmol) of trans-1,4-dibromo-2-butene and 240 mL of THF (super dehydrated) were added into the flask and the flask was stirred for 30 minutes. Thereafter, the flask was placed in ice bath for 15 minutes in order to perform sufficient cooling while continuing to stir the flask. The flask was held in the ice bath while using the dropping funnel to drip in, over a period of 200 minutes, a THF (120 mL) solution of 8.0 g (13.14 mmol) of 1,3-bis[(1-adamantyloxy)carbonyloxy]adamantane (Ad3) that had been separately prepared in a degassing dried vessel. (Note that the dripping time is proportional to the charged amount and is for example 25 minutes in the case of addition of 1.0 g of 1,3-bis[(1-adamantyloxy)carbonyloxy]adamantane (Ad3).) After the dripping, the ice bath was removed and a reaction was carried out for 3 hours at 70° C. while stirring the flask. The reaction was tracked using TLC and LC-MS. After the reaction, the flask was cooled to room temperature and 360 mL of water was gradually added to the flask in order to quench excess sodium hydride. This operation was extremely dangerous because it led to production of a large amount of hydrogen gas and generation of heat, and was therefore performed with the flask in an ice bath and open to the atmosphere. Filtration was performed and subsequently an evaporator was used to evaporate only the THF. Next, 360 mL of diethyl ether was added to the resultant residue, the residue was transferred to a separating funnel (1,000 mL), and extraction was performed. In the extraction, an aqueous layer was first removed and then three extraction operations were performed using 400 mL of a saturated aqueous solution of sodium hydrogen carbonate and four extraction operations were performed using 400 mL of a saturated aqueous solution of sodium chloride. The organic layer was collected, dried for 30 minutes using magnesium sulfate (anhydrous), and filtered. Thereafter, solvent was evaporated using an evaporator and a vacuum pump to obtain a crude product as a solid. The resultant crude product was purified by column chromatography (silica gel). The column chromatography was performed using a flash column having a column tube diameter of 90 cm. In the column chromatography, the silica gel had a height of 250 mm (mass of silica gel approximately 900 g) and 10:1 n-hexane:ethyl acetate was used as a developing solvent. The crude product was dissolved in 30 mL of the developing solvent. Pressure was applied using a double bulb pump. The presence of the product in the resultant solution was confirmed by TLC. Solvent was completely evaporated from the solution that has passed through the column using an evaporator and a vacuum pump to obtain the product (1,3-bis[(1-adamantyloxycarbonyl-2-vinylcyclopropane-1-yl)carbonyloxy]adamantane (Ad-MVCP); compound represented by structural formula (6) shown below) as a white solid. The structure of the product was evaluated by NMR (FIGS. 7 and 8), Fourier transform infrared spectroscopy (FT-IR) (FIG. 9), and LC-MS (FIG. 10), and the purity of the product was obtained from the area ratio in LC-MS (yield 49.6%, purity 100.0%).

[CHEM. 13]

(6)

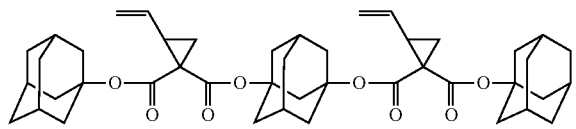

The 1,3-bis[(1-adamantyloxycarbonyl-2-vinylcyclopropane-1-yl)carbonyloxy]adamantane (Ad-MVCP) obtained as described above was evaluated by the following methods for (i) volume change upon polymerization, (ii) dynamic viscoelasticity of a polymer having the obtained monomer as a constituent component, (iii) solubility of the obtained monomer, and (iv) heat resistance of a polymer having the obtained monomer as a constituent component. The evaluation results are shown below in Tables 1-4.

<(i) Evaluation of Volume Change Upon Polymerization>

First, polymerization of the obtained monomer (compound represented by structural formula (6)) was performed as follows.

A freezing ampoule (20 mL) was charged with 4.03 mg of AIBN (4 mol %), 440.2 mg (0.61 mmol) of Ad-MVCP, and 0.267 g (0.31 mL) of toluene, and the monomer was dissolved. Thereafter, freeze drying was performed three times and dissolved oxygen was removed. The freezing ampoule was immersed in an oil bath and was heated for 48 hours at 60° C. to polymerize the monomer. After polymerization, the freezing ampoule was cooled by liquid nitrogen to quench radicals. Next, 50 mL of toluene was added to the freezing ampoule in order to dissolve undissolved components other than the polymer and suction filtration was then performed. Polymer filtered onto filter paper as a result was washed with toluene and acetone, was vacuum dried for 48 hours at 100° C., and was collected as a white solid polymer. The collected polymer was used as an evaluation sample.

Figure 11:
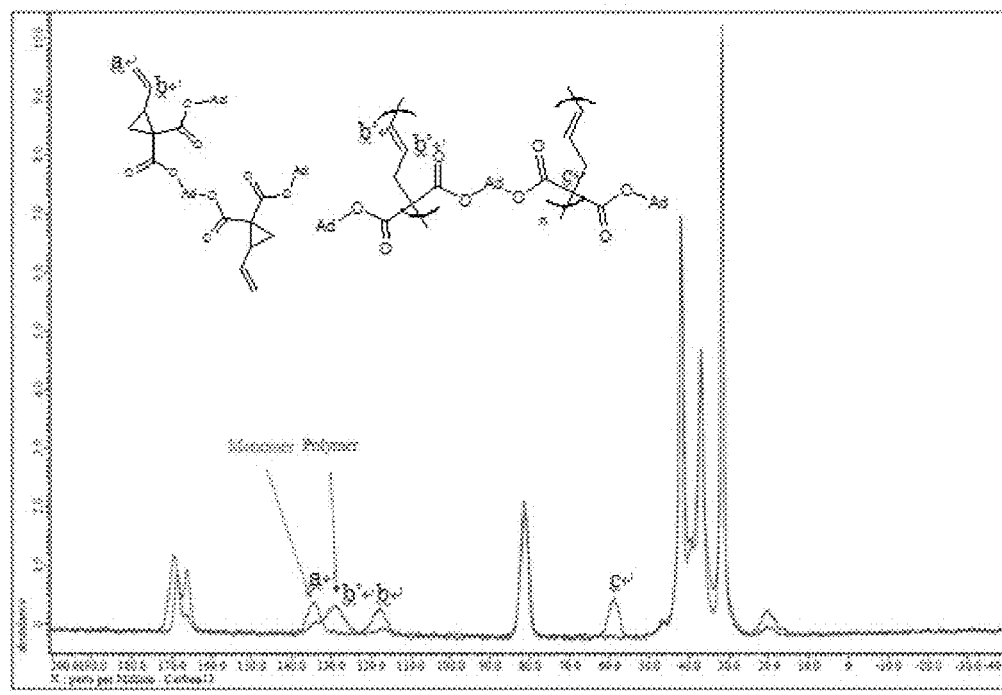
FIG. 11 is a cross polarization magic angle spinning (CP-MAS) chart of a 1,3-bis[(1-adamantyloxycarbonyl-2-vinylcyclopropane-1-yl)carbonyloxy]adamantane (Ad-MVCP) monomer in Example 1 and a polymer having the obtained monomer as a constitutional component.

The polymer had formed a network and was insoluble in solvent. Therefore, confirmation of whether the polymer had a 1,5-ring-opened structure was performed by $^{13}$C-NMR (CP-MAS) (FIG. 11).

<<Calculation of Volume Change Upon Polymerization>>

The volume change upon polymerization was calculated using the following equation by measuring the monomer density and polymer density of each sample prepared by the procedure described above using a dry automatic pycnometer (AccuPyc II 1340 produced by Shimadzu Corporation).

((Monomer density)−(Polymer density))/(Monomer density)×100(%)

A positive calculated value indicates volume expansion whereas a negative calculated value indicates volume shrinkage.

<(ii) Evaluation of Polymer Dynamic Viscoelasticity>

The obtained monomer was homogenized with 0.5 parts by mass of PERHEXA HC (producer: NOF Corporation) and 0.2 mL of acetone added thereto, was subsequently poured into a 10 mm×40 mm×0.5 mm silicone rubber sheet mold prepared on an aluminum plate, and was transferred into a vacuum oven. Acetone solvent was first vaporized while maintaining the temperature at room temperature and the pressure at 20 cmHg to 40 cmHg, and thereafter the pressure was restored to normal pressure and curing was performed for 5 hours at 140° C. to prepare a cured product. The cured product that was prepared was evaluated by measurement as described below using a tension mode of a dynamic mechanical analyzer (DMA).

The cured product was set in the dynamic mechanical analyzer (producer: TA Instruments, product name: RSA3) and the device was used to measure the storage modulus (E') in a temperature range of from 30° C. to 300° C. with a heating rate of 10.0° C./min. Furthermore, the temperature corresponding to a maximum value of tan δ (loss modulus/storage modulus) obtained under a measurement condition of a frequency of 11.0 Hz was taken to be the glass-transition temperature (Tg).

<(iii) Evaluation of Monomer Solubility>

The solubility of 40 mg of the obtained monomer in 1.0 mL of various solvents (methyl ethyl ketone (MEK), acetone, propylene glycol monomethyl ether acetate (PG-MEA), and cyclohexanone) was evaluated.

<(iv) Evaluation of Polymer Heat Resistance>

Heat resistance of the polymer used in (i) evaluation of volume change upon polymerization was evaluated using a thermogravimetric analyzer (producer: Seiko Instruments Incorporated, product name: EXSTAR6000). Furthermore, thermogravimetric change of the obtained polymer was measured to obtain a temperature at which a 10% reduction in weight was reached and the 10% weight loss temperature was taken to be the pyrolysis temperature ($Td^{10}$).

Comparative Example 1

Evaluation of (i) volume change upon polymerization and (ii) polymer dynamic viscoelasticity was performed in the same way as in Example 1 with the exception that the synthesized 1,3-bis[(1-adamantyloxycarbonyl-2-vinylcyclopropane-1-yl)carbonyloxy]adamantane (Ad-MVCP) used in Example 1 was replaced with tricyclodecane dimethanol dimethacrylate represented by structural formula (10) shown below (producer: Shin-Nakamura Chemical Co., Ltd., product name: NK Ester DCP). The evaluation results are shown below in Tables 1-3.

[CHEM. 14]

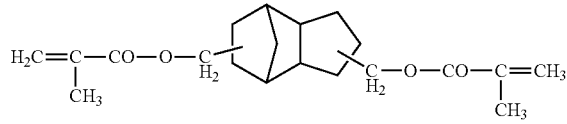

(10)

Note that in Comparative Example 1, the resultant polymer was purified by dissolving the polymer in 20 mL of dichloromethane, pouring the resultant solution into 200 mL of methanol to produce a precipitate, and performing re-precipitation of the produced white polymer three times. Thereafter, vacuum drying was performed for 48 hours while heating at 100° C. and a white solid polymer was collected. The collected polymer was used as an evaluation sample.

Comparative Example 2

Evaluation of (i) volume change upon polymerization, (ii) polymer dynamic viscoelasticity, (iii) monomer solubility, and (iv) polymer heat resistance was performed in the same way as in Example 1 with the exception that the synthesized 1,3-bis[(1-adamantyloxycarbonyl-2-vinylcyclopropane-1-yl)carbonyloxy]adamantane (Ad-MVCP) used in Example 1 was replaced with 1,1-bis[(1-adamantyloxy)carbonyl]-2-vinylcyclopropane (Ad-VCP) represented by structural formula (5) shown below. The evaluation results are shown below in Tables 1, 3, and 4.

The Ad-VCP used herein was synthesized based on the description in Ueda et al., Macromolecules, 27, 5543 (1994).

Note that in Comparative Example 2, the resultant polymer was purified by dissolving the polymer in 20 mL of dichloromethane, pouring the resultant solution into 200 mL of methanol to produce a precipitate, and performing re-precipitation of the produced white polymer three times. Thereafter, vacuum drying was performed for 48 hours while heating at 100° C. and a white solid polymer was collected. The collected polymer was used as an evaluation sample.

[CHEM. 15]

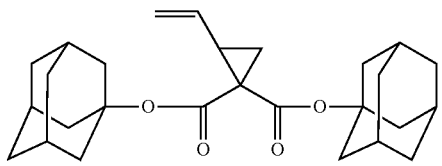

(5)

Comparative Example 3

Evaluation of (i) volume change upon polymerization was performed in the same way as in Example 1 with the exception that the synthesized 1,3-bis[(1-adamantyloxycarbonyl-2-vinylcyclopropane-1-yl)carbonyloxy]adamantane (Ad-MVCP) used in Example 1 was replaced with 1,3-bis [(1-methoxycarbonyl-2-vinylcyclopropane-1-yl)carboxy] benzene (Me-MVCP) represented by structural formula (1) shown below. The evaluation results are shown below in Table 1.

The Me-MVCP used herein was synthesized based on the description in N. Moszner et al., Journal of Applied Polymer Science, 72, 1775 (1999).

Note that in Comparative Example 3, polymerization of the monomer was performed by bulk polymerization based on the aforementioned document. A freezing ampoule (20 mL) was charged with 15.8 mg (0.096 mmol) of AIBN and 1.000 g (2.41 mmol) of Me-MVCP, and the monomer was dissolved. Thereafter, freeze drying was performed three times and dissolved oxygen was removed. The freezing ampoule was immersed in an oil bath and was heated for 48 hours at 60° C. to polymerize the monomer. After polymerization, the freezing ampoule was cooled by liquid nitrogen to quench radicals. Next, 50 mL of toluene was added to the freezing ampoule in order to dissolve undissolved components other than the polymer and suction filtration was then performed. Polymer filtered onto filter paper as a result was sufficiently washed with toluene and acetone, was vacuum dried for 48 hours while heating at 100° C., and was collected as a white solid polymer. The collected polymer was used as an evaluation sample.

[CHEM. 16]

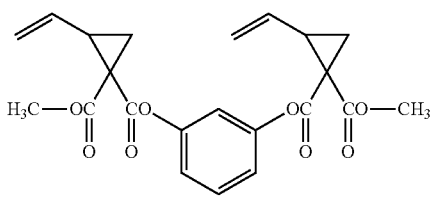

(1)

Example 2

Evaluation of (i) volume change upon polymerization was performed in the same way as in Example 1 with the exception that instead of using the synthesized 1,3-bis[(1-adamantyloxycarbonyl-2-vinylcyclopropane-1-yl)carbonyloxy]adamantane mantane (Ad-MVCP) individually, two types of monomers in the form of Ad-MVCP and tricyclodecane dimethanol dimethacrylate (DCP) (producer: Shin-Nakamura Chemical Co., Ltd., product name: NK Ester DCP) were used in equal amounts (mmol). The evaluation results are shown below in Table 2.

Note that in Example 2, 0.159 g (0.479 mmol) of DCP, 0.341 g (0.479 mmol) of Ad-MVCP, and 0.2 mL of toluene (dehydrated) were added into an ampoule with a stirrer, were heated to 70° C., and were homogenized by stirring. After performing cooling to room temperature, a dilute solution of AIBN (6.3 mg (0.038 mmol) of AIBN dissolved in 0.28 mL of toluene (dehydrated)) was added to the ampoule. The ampoule was sealed using a gas burner after performing freeze degassing of the ampoule. The ampoule was immersed in an oil bath and a reaction was carried out for 48 hours at 60° C. After the reaction, the ampoule was immersed in liquid nitrogen and a polymer was collected. The resultant polymer was sufficiently washed with toluene and acetone and was vacuum dried for 48 hours while heating at 100° C., and a white solid polymer was collected. The collected polymer was used as an evaluation sample.

Furthermore, a sample for monomer density evaluation was prepared as follows in Example 2.

<Preparation of Monomer Density Evaluation Sample>

Ad-MVCP in an amount of 0.153 g (0.215 mmol) and DCP in an amount of 0.072 g (0.216 mmol) were dissolved and homogenized in 0.3 mL of acetone. After removing the acetone, vacuum drying was performed for 72 hours at room temperature, and the resultant monomers were then used as a sample for density evaluation.

Example 3

Evaluation of (i) volume change upon polymerization was performed in the same way as in Example 2 with the exception that instead of using equal amounts of DCP and Ad-MVCP as monomers as in Example 2, DCP and Ad-MVCP were used with a monomer ratio of 1:2. The evaluation results are shown below in Table 2.

Example 4

Evaluation of (i) volume change upon polymerization was performed in the same way as in Example 2 with the exception that instead of using equal amounts of DCP and Ad-MVCP as monomers as in Example 2, DCP and Ad-MVCP were used with a monomer ratio of 1:3. The evaluation results are shown below in Table 2.

(Evaluation Results for Volume Change Resulting from Homopolymerization)

Table 1 shows the evaluation results for volume change resulting from homopolymerization in Comparative Examples 1-3 and Example 1.

TABLE 1

|  | DCP (%) | Ad-VCP (%) | Me-MVCP (%) | Ad-MVCP (%) | Conversion rate (%) | Monomer density (g/cm$^3$) | Polymer density (g/cm$^3$) | Volume change (%) |
|---|---|---|---|---|---|---|---|---|
| Comparative Example 1 | 100 | 0 | 0 | 0 | 89.4 | 1.101 | 1.194 | −8.5 |
| Comparative Example 2 | 0 | 100 | 0 | 0 | 99.0 | 1.178 | 1.127 | +4.3 |
| Comparative Example 3 | 0 | 0 | 100 | 0 | 83.5 | — | — | −9.5 |
| Example 1 | 0 | 0 | 0 | 100 | 98.0 | 1.275 | 1.198 | +6.1 |

It was confirmed that the volume change resulting from homopolymerization of DCP in Comparative Example 1 was −8.5%, indicating shrinkage, whereas the volume change resulting from homopolymerization of the vinylcyclopropane (Ad-MVCP) in Example 1 was +6.1%, indicating volume expansion. The volume change resulting from homopolymerization of the monofunctional vinylcyclopropane Ad-VCP in Comparative Example 2, which had adamantyl groups as substituents, was +4.3% as is commonly known from the literature, indicating volume expansion. However, the value of +6.1% for the multifunctional structure in Example 1 exceeded the value of +4.3% in Comparative Example 2. It should be noted that a multifunctional vinylcyclopropane that exhibits a large degree of volume expansion as in Example 1 is not commonly known.

(Evaluation Results for Volume Change Resulting from Copolymerization)

Since it was confirmed that a volume expansion of +6.1% was exhibited in Example 1, in Examples 2-4 in which the vinylcyclopropane (Ad-MVCP) of Example 1 was copolymerized in equal, double, and triple amounts, respectively, with the DCP of Comparative Example 1 that exhibited shrinkage (−8.5%), it was confirmed whether the degree of shrinkage was reduced as a result of the vinylcyclopropane (Ad-MVCP) of Example 1 being contained as a constituent component of the copolymer. Table 2 shows the evaluation results for volume change resulting from copolymerization in Comparative Example 1 and Examples 1-4.

TABLE 2

| | DCP (%) | Ad-VCP (%) | Me-MVCP (%) | Ad-MVCP (%) | Conversion rate (%) | Monomer density (g/cm$^3$) | Polymer density (g/cm$^3$) | Volume change (%) |
|---|---|---|---|---|---|---|---|---|
| Comparative Example 1 | 100 | 0 | 0 | 0 | 89.4 | 1.101 | 1.194 | −8.5 |
| Example 1 | 0 | 0 | 0 | 100 | 98.0 | 1.275 | 1.198 | +6.1 |
| Example 2 (equal amount) | 50 | 0 | 0 | 50 | 98.0 | 1.134 | 1.187 | −4.7 |
| Example 3 (double amount) | 33 | 0 | 0 | 67 | 99.5 | 1.140 | 1.189 | −4.3 |
| Example 4 (triple amount) | 25 | 0 | 0 | 75 | 99.8 | 1.144 | 1.185 | −3.6 |

Through comparison of Examples 2-4, it was confirmed that the degree of polymerization shrinkage decreased with increasing amount of the vinylcyclopropane (Ad-MVCP) included as a constituent component of the copolymer.

(Evaluation Results for Dynamic Viscoelasticity)

Table 3 shows the results for dynamic viscoelasticity of the polymers in Example 1 and Comparative Examples 1 and 2.

TABLE 3

| | E' (Pa) | | | | |
|---|---|---|---|---|---|
| | 50° C. | 120° C. | 140° C. | 160° C. | Tg (° C.) |
| Comparative Example 1 | 1.70 × 10$^9$ | 9.60 × 10$^8$ | 8.00 × 10$^8$ | 6.60 × 10$^8$ | >271.1 |
| Comparative Example 2 | — | — | — | — | 23 |
| Example 1 | 1.10 × 10$^9$ | 7.40 × 10$^8$ | 6.60 × 10$^8$ | 7.00 × 10$^8$ | 235 |

The homopolymer of the vinylcyclopropane (Ad-MVCP) in Example 1 exhibited similar characteristics to the homopolymer of DCP in Comparative Example 1 at temperatures around room temperature and exhibited superior characteristics to the homopolymer of DCP in Comparative Example 1 under high-temperature conditions. These results demonstrate that the homopolymer of the vinylcyclopropane (Ad-MVCP) in Example 1 can be used as an alternative or additive material for acrylic compounds that exhibit polymerization shrinkage with an objective of reducing the degree of shrinkage.

(Evaluation Results for Monomer Solubility)

Table 4 shows evaluation results for monomer solubility of monomer compounds that contained adamantyl groups (Comparative Example 2 and Example 1).

TABLE 4

| Solubility | Comparative Example 2 | Example 1 |
|---|---|---|
| MEK | Poor | Excellent |
| Acetone | Poor | Excellent |
| PGMEA | Poor | Excellent |
| Cyclohexanone | Mediocre | Excellent |

The vinylcyclopropane (Ad-MVCP) in Example 1 (multifunctional monomer) exhibited superior monomer solubility in solvents in which the Ad-VCP in Comparative Example 2 (monofunctional monomer) did not dissolve.

(Evaluation Results for Heat Resistance)

When heat resistance of the polymers in Comparative Example 2 and Example 1 was evaluated, the homopolymer of the vinylcyclopropane (Ad-MVCP) in Example 1 exhibited a Td$^{10}$ of 399° C. compared to a Td$^{10}$ of 361° C. exhibited by the homopolymer of Ad-VCP in Comparative Example 2. These results demonstrate that the homopolymer of the vinylcyclopropane (Ad-MVCP) in Example 1 has superior heat resistance to the homopolymer of Ad-VCP in Comparative Example 2. The homopolymer of the vinylcyclopropane (Ad-MVCP) in Example 1 is thought to have improved heat resistance as a result of formation of a network structure with the adamantyl groups.

<$^1$H-NMR Analysis Results in FIG. 1>
$^1$H-NMR (CDCl$_3$) δ 1.66 ppm (m, 6H, adamantyl), 2.10 ppm to 2.20 ppm (m, 9H, adamantyl), 3.50 ppm (s, 2H, —OOCCH$_2$COO—), 11.34 ppm (s, 1H, —COOH)

Figure 2:
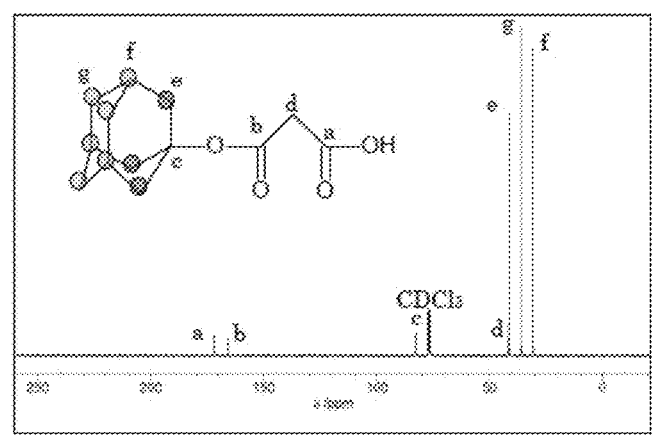
FIG. 2 is a $^{13}$C-NMR chart of O-adamantylmalonic acid (Ad-COOH) in Example 1.

<$^{13}$C-NMR Analysis Results in FIG. 2>
$^{13}$C-NMR (CDCl$_3$) δ 30.77 ppm (C-f), 35.90 ppm (C-g), 40.95 ppm (C-e), 42.03 ppm (C-d), 82.85 ppm (C-c), 165.77 ppm (C-b), 171.94 ppm (C-a)

Figure 3:
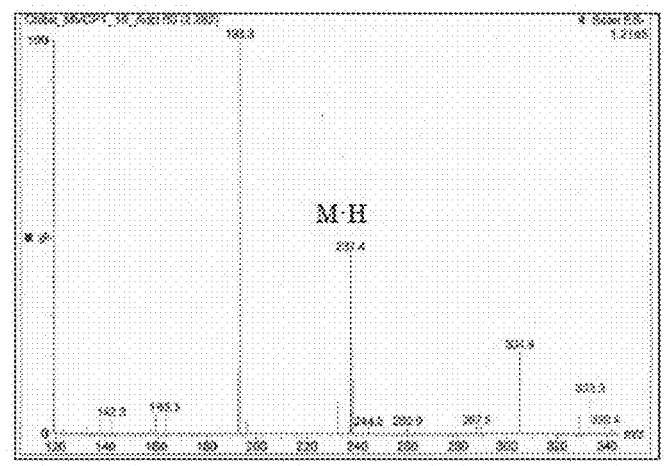
FIG. 3 is a liquid chromatography-mass spectrometry (LC-MS) chart of O-adamantylmalonic acid (Ad-COOH) in Example 1.

<LC-MS Analysis Results in FIG. 3>
m/z: 237.4 (M−H)

Figure 4:
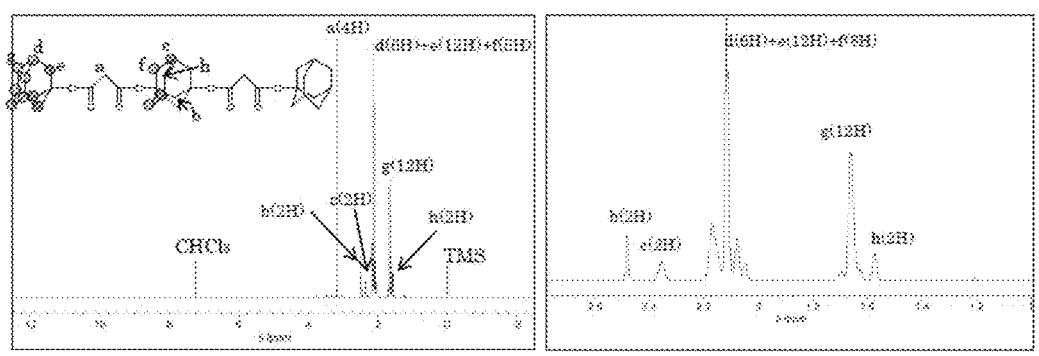
FIG. 4 is a $^1$H-NMR chart of 1,3-bis[(1-adamantyloxy)carbonyloxy]adamantane (Ad3) in Example 1.

<$^1$H-NMR Analysis Results in FIG. 4>
$^1$H-NMR (CDCl$_3$) δ 1.57 ppm (s, 2H, adamantyl), 1.60 ppm to 1.70 ppm (m, 12H, adamantyl), 2.00 ppm to 2.20 ppm (m, 26H, adamantyl), 2.36 ppm (s, 2H, adamantyl), 2.48 ppm (s, 2H, adamantyl), 3.18 ppm (s, —OOCCH$_2$COO—, 4H)

Figure 5:
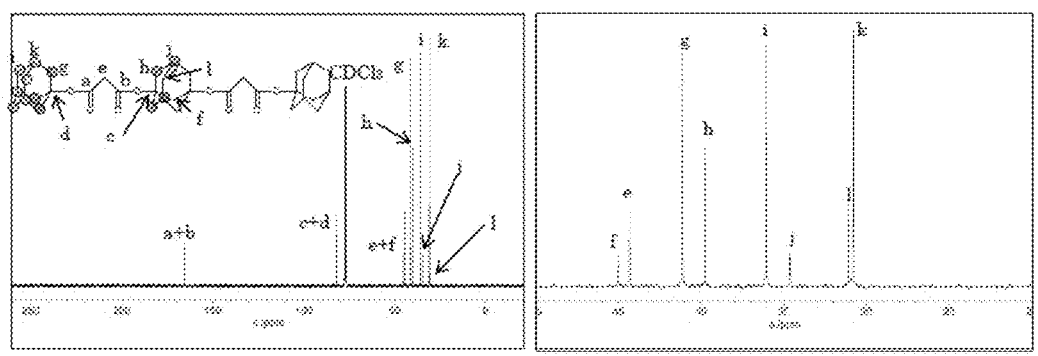
FIG. 5 is a $^{13}$C-NMR chart of 1,3-bis[(1-adamantyloxy)carbonyloxy]adamantane (Ad3) in Example 1.

<$^{13}$C-NMR Analysis Results in FIG. 5>
$^{13}$C-NMR (CDCl$_3$) δ 30.08 ppm (C-k), 31.10 ppm (C-l), 34.64 ppm (C-j), 36.08 ppm (C-i), 39.77 ppm (C-h), 41.13 ppm (C-g), 44.32 ppm (C-e), 45.01 ppm (C-f), 81.77 ppm and 81.85 ppm (C-c/d), 165.07 ppm (C-a/b)

Figure 6:
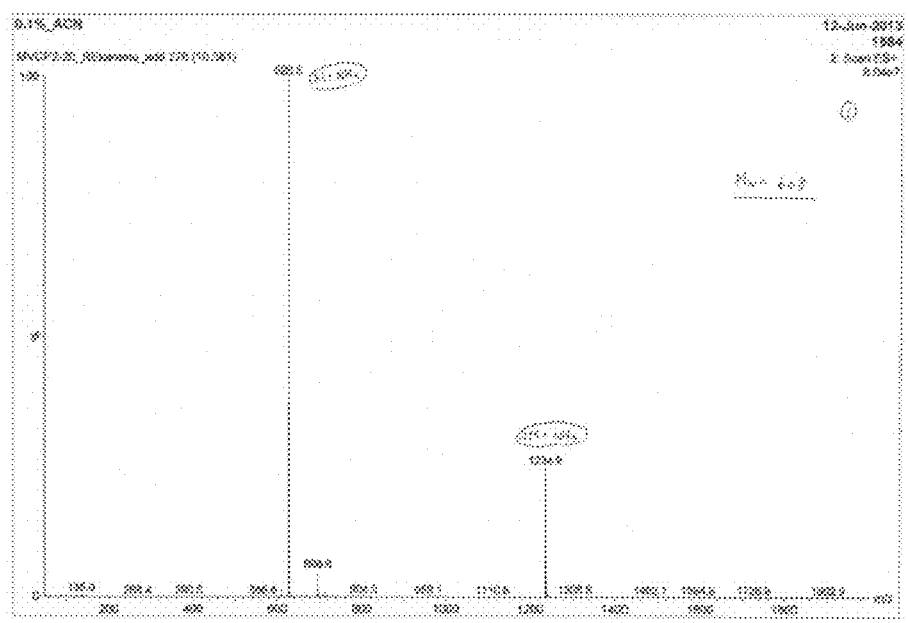
FIG. 6 is an LC-MS chart of 1,3-bis[(1-adamantyloxy)carbonyloxy]adamantane (Ad3) in Example 1.

<LC-MS Analysis Results in FIG. 6>
m/z: 1234.9 (2M+NH$_4$), 625.5 (M+NH$_4$)

Figure 7:
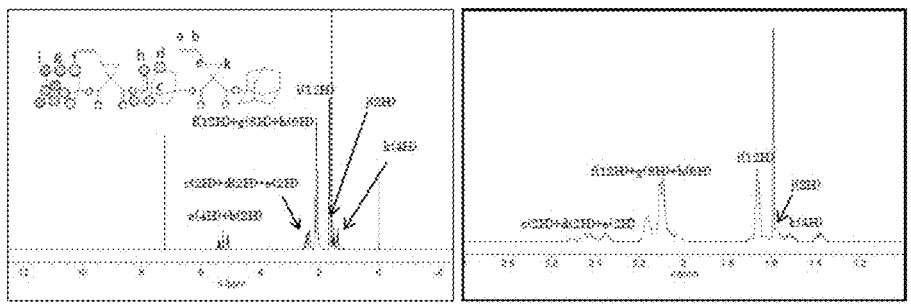
FIG. 7 is a $^1$H-NMR chart of 1,3-bis[(1-adamantyloxycarbonyl-2-vinylcyclopropane-1-yl)carbonyloxy]adamantane (Ad-MVCP) in Example 1.

<$^1$H-NMR Analysis Results in FIG. 7>
$^1$H-NMR (CDCl$_3$) δ 1.35 ppm to 1.54 ppm (m, HCH< of cyclopropane, 4H), 1.57 ppm (s, 2H, adamantyl), 1.60 ppm to 1.70 ppm (m, adamantyl, 12H), 2.00 ppm to 2.20 ppm (m, adamantyl and CH< of cyclopropane, 6H+12H+8H), 5.08 ppm to 5.50 ppm (m, HCH=CH and CH$_2$=CH, 6H)

Figure 8:
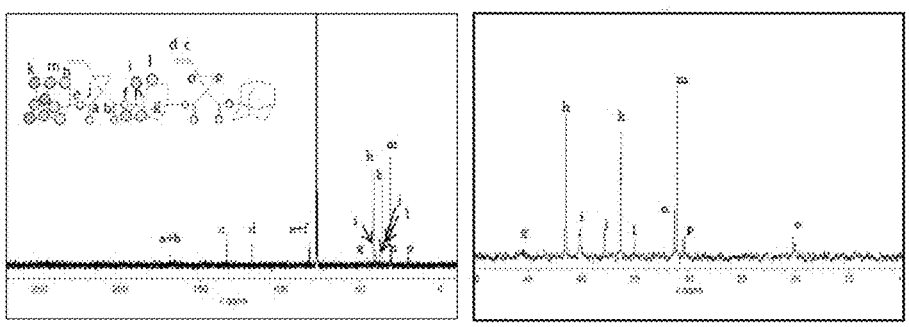
FIG. 8 is a $^{13}$C-NMR chart of 1,3-bis[(1-adamantyloxycarbonyl-2-vinylcyclopropane-1-yl)carbonyloxy]adamantane (Ad-MVCP) in Example 1.

<$^{13}$C-NMR Analysis Results in FIG. 8>
$^{13}$C-NMR (CDCl$_3$) δ 20.09 ppm (C-o), 30.02 ppm (C-p), 30.95 ppm (C-m), 31.27 ppm (C-n), 34.90 ppm (C-l), 36.28 ppm (C-k), 37.80 ppm (C-j), 40.09 ppm (C-i), 41.41 ppm (C-h), 45.36 ppm (C-g), 81.71 ppm and 82.02 ppm (C-e/f), 117.95 ppm (C-d), 133.62 ppm (C-c), 166.57 ppm and 168.89 ppm (C-a/b)

Figure 9:
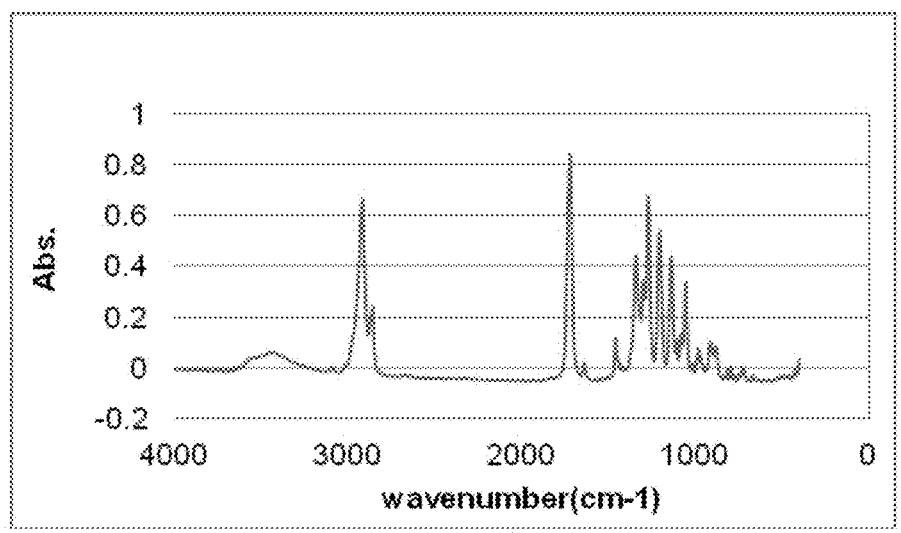
FIG. 9 is a Fourier transform infrared spectrophotometer (FT-IR) chart of 1,3-bis[(1-adamantyloxycarbonyl-2-vinylcyclopropane-1-yl)carbonyloxy]adamantane (Ad-MVCP) in Example 1.

<IR Analysis Results (Cm$^{−1}$) in FIG. 9>
FT-IR (KBr): 1702 cm$^{−1}$ (C=O), 1639 cm$^{−1}$ (C=C)

Figure 10:
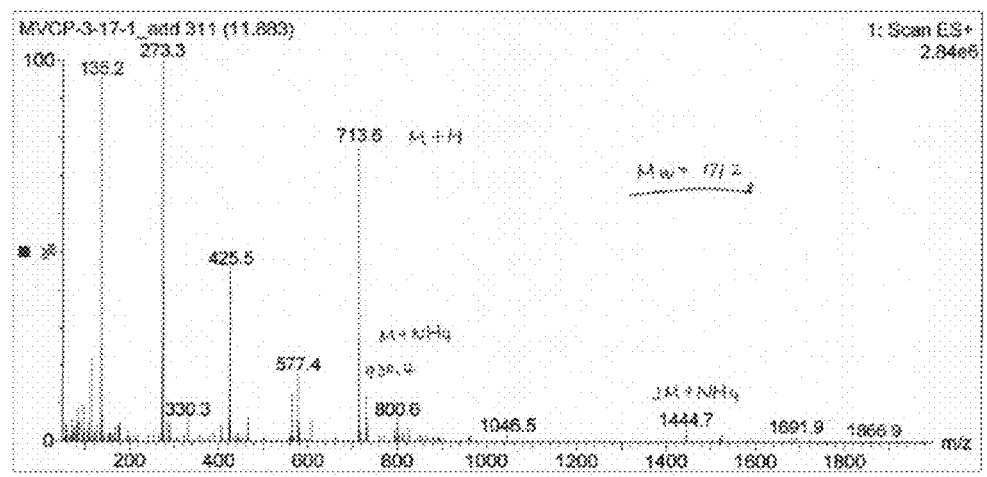
FIG. 10 is an LC-MS chart of 1,3-bis[(1-adamantyloxycarbonyl-2-vinylcyclopropane-1-yl)carbonyloxy]adamantane (Ad-MVCP) in Example 1.

<LC-MS Analysis Results in FIG. 10>
m/z: 1444.7 (2M+NH$_4$), 730.4 (M+NH$_4$), 713.6 (M+H)

<CP-MAS Analysis Results in FIG. 11>
Monomer: 14.34 ppm to 24.78 ppm, 24.78 ppm to 52.03 ppm, 78.60 ppm to 85.24 ppm, 113.83 ppm to 123.61 ppm, 130.80 ppm to 139.54 ppm, 162.51 ppm to 170.0 ppm Polymer: 17.77 ppm to 24.02 ppm, 24.02 ppm to 50.98 ppm, 56.10 ppm to 64.84 ppm, 77.54 ppm to 84.96 ppm, 114.45 ppm to 139.06 ppm, 164.84 ppm to 173.44 ppm

INDUSTRIAL APPLICABILITY

The presently disclosed vinylcyclopropane can be suitably used in production of optical materials, molding materials, composite materials, casting materials, sealing materials, medical materials, dental materials, recording materials, cements, coating materials, adhesives, materials for holographic optical recording media, and so forth.

The invention claimed is:

1. A vinylcyclopropane represented by general formula (I) shown below

[CHEM. 1]

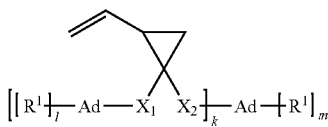

(I)

where, in general formula (I):
$R^1$ represents —H, —OH, —$NH_2$, —$NO_2$, —COOR, —CN, =O, —OCOCH=$CH_2$, —OCO($CH_3$)C=$CH_2$, a halogen, an alkylene group having a carbon number of 1-20, a cycloalkylene group having a carbon number of 3-20, an arylene group having a carbon number of 6-14, or any one of an alkylene group having a carbon number of 1-20, a cycloalkylene group having a carbon number of 3-20, or an arylene group having a carbon number of 6-14 interrupted by O, S, N, or NH;
$X_1$ represents CO, CO—O, O—CO, CO—S, S—CO, CO—NR, NR—CO, O, S, $SO_2$, or a single bond;
$X_2$ represents CO, CO—O, O—CO, CO—S, S—CO, CO—NR, NR—CO, O, S, $SO_2$, or a single bond;
for $R^1$, $X_1$, and $X_2$, R represents H, an alkyl group having a carbon number of 1-6, a cycloalkylene group having a carbon number of 3-6, an aryl group having a carbon number of 6-14, or a heterocyclic group having a carbon number of 6-14;
k represents an integer of 2-4;
l represents an integer of 1-9;
m represents an integer of 1-8; and
Ad represents an adamantyl group.
2. The vinylcyclopropane of claim 1, wherein $X_1$ and $X_2$ are each an ester.
3. The vinylcyclopropane of claim 1, wherein k is 2.
4. A monomer composition comprising the vinylcyclopropane of claim 1.
5. A monomer composition comprising the vinylcyclopropane of claim 3.
6. A polymer of the vinylcyclopropane of claim 1.
7. A polymer of the vinylcyclopropane of claim 3.
8. The polymer of claim 6, wherein
the polymer exhibits a volume change of at least +5.0% relative to monomer volume of the vinylcyclopropane.
9. The polymer of claim 6, wherein
the polymer is a copolymer of the vinylcyclopropane and a polymerizable compound other than the vinylcyclopropane.
10. A polymer composition comprising the polymer of claim 6.
11. A polymer composition comprising the polymer of claim 7.
12. A polymer composition comprising the polymer of claim 8.
13. A polymer composition comprising the polymer of claim 9.
14. An article obtainable through curing of the monomer composition of claim 4.
15. An article obtainable through curing of the monomer composition of claim 5.

* * * * *